United States Patent
Kakaulin et al.

(10) Patent No.: US 10,417,715 B1
(45) Date of Patent: Sep. 17, 2019

(54) COMPUTER ARCHITECTURES AND ASSOCIATED METHODS FOR ENABLING REAL-TIME DATA DETERMINATIONS AND DISTRIBUTION

(71) Applicant: Hippo Technologies LLC, New York, NY (US)

(72) Inventors: Eugene Kakaulin, New York, NY (US); Michael Tanenbaum, New York, NY (US); Andrew Stead, New York, NY (US); Eric Young, New York, NY (US)

(73) Assignee: Hippo Technologies LLC, New York, NY (US)

( * ) Notice: Subject to any disclaimer, the term of this patent is extended or adjusted under 35 U.S.C. 154(b) by 0 days.

(21) Appl. No.: 15/897,083

(22) Filed: Feb. 14, 2018

(51) Int. Cl.
| | |
|---|---|
| *G06Q 40/08* | (2012.01) |
| *G16H 20/10* | (2018.01) |
| *G06F 3/0482* | (2013.01) |
| *G06Q 20/40* | (2012.01) |
| *G06F 16/29* | (2019.01) |

(52) U.S. Cl.
CPC ........... *G06Q 40/08* (2013.01); *G06F 3/0482* (2013.01); *G06F 16/29* (2019.01); *G06Q 20/40* (2013.01); *G16H 20/10* (2018.01)

(58) Field of Classification Search
CPC ........ G06Q 40/08; G06Q 20/40; G16H 40/20; G16H 20/10; G06F 16/29; G06F 3/0482
See application file for complete search history.

(56) References Cited

U.S. PATENT DOCUMENTS

| | | |
|---|---|---|
| 7,711,577 B2 | 5/2010 | Dust et al. |
| 7,734,483 B1 | 6/2010 | Smith et al. |
| 7,743,979 B2 | 6/2010 | Fredman |

(Continued)

FOREIGN PATENT DOCUMENTS

| | | | |
|---|---|---|---|
| CA | 2531875 A1 * | 7/2006 | ............ G06Q 10/10 |
| WO | WO-2014/145170 A1 | 9/2014 | |

OTHER PUBLICATIONS

American Pharmacist Association (ApPhA): HIPPA; National Provider Identifier (NPI), Mar. 14-17, 2008, APhA 2008 SanDiego Annual Meeting Expositions, pp. 1-3. (Year: 2008).*

(Continued)

*Primary Examiner* — Bijendra K Shrestha
(74) *Attorney, Agent, or Firm* — Wilmer Cutler Pickering Hale and Dorr LLP

(57) ABSTRACT

Computer architectures and associated methods for real-time data processing are disclosed. In some embodiments, a trial adjudication request for a cost determination can be received by a first server and verified using a security protocol, wherein a password token of the trial adjudication request can be matched to a stored password token. The first server can transmit an adjudication command packet to a second server that includes at least one data set of a plurality of data sets and a command for a claim determination, and can receive a response packet from the second server. The first server can determine that a successful claim determination was performed by the second server from the response packet, and can transmit a reversal request packet to the second server which can cancel the successful claim determination. The first server can perform the electronic calculation using the claim data.

19 Claims, 6 Drawing Sheets

(56) References Cited

U.S. PATENT DOCUMENTS

| | | | |
|---|---|---|---|
| 7,912,741 B1* | 3/2011 | Pinsonneault | G06Q 10/10 600/300 |
| 7,917,372 B2 | 3/2011 | Oscar et al. | |
| 7,957,983 B2 | 6/2011 | Hoffman et al. | |
| 8,036,916 B2 | 10/2011 | Dust et al. | |
| 8,082,173 B2 | 12/2011 | Kost et al. | |
| 8,099,295 B2 | 1/2012 | Virdee et al. | |
| 8,112,287 B1 | 2/2012 | Paul et al. | |
| 8,112,288 B1 | 2/2012 | Paul et al. | |
| 8,296,164 B2 | 10/2012 | Oscar et al. | |
| 8,380,540 B1 | 2/2013 | Smith et al. | |
| 8,521,551 B1 | 8/2013 | Paul et al. | |
| 8,521,557 B1* | 8/2013 | Ringold | G06Q 30/0207 705/2 |
| 8,626,524 B1 | 1/2014 | Koehl et al. | |
| 8,670,991 B2 | 3/2014 | Kost et al. | |
| 8,670,996 B1 | 3/2014 | Weiss | |
| 8,683,562 B2* | 3/2014 | Ting | G06F 21/35 726/6 |
| 8,706,522 B2 | 4/2014 | Cohan et al. | |
| 8,712,797 B1 | 4/2014 | Bezdek et al. | |
| 8,738,399 B1 | 5/2014 | Abou Nader et al. | |
| 9,773,094 B1 | 9/2017 | Balagere et al. | |
| 9,786,023 B2 | 10/2017 | Cohan et al. | |
| 2002/0110136 A1* | 8/2002 | Wakai | H04L 45/00 370/419 |
| 2006/0229932 A1 | 10/2006 | Zollo et al. | |
| 2007/0018794 A1* | 1/2007 | Bares | G06F 1/12 340/10.3 |
| 2007/0133591 A1* | 6/2007 | Shatford | H04L 63/0442 370/457 |
| 2009/0157748 A1 | 6/2009 | Hess | |
| 2010/0070757 A1* | 3/2010 | Martinez | H04L 63/0846 713/155 |
| 2012/0185263 A1 | 7/2012 | Emert | |
| 2013/0151281 A1 | 6/2013 | Kaburick et al. | |
| 2013/0219473 A1* | 8/2013 | Schaefer | G06F 21/335 726/4 |
| 2014/0201021 A1 | 7/2014 | Begley et al. | |
| 2014/0244307 A1 | 8/2014 | Shutko et al. | |
| 2014/0244546 A1 | 8/2014 | Bezdek et al. | |
| 2014/0278482 A1 | 9/2014 | Shah | |
| 2014/0324447 A1 | 10/2014 | Dittus | |
| 2015/0128532 A1 | 5/2015 | Miller et al. | |
| 2015/0222479 A1* | 8/2015 | Kim | H04W 28/0236 370/218 |
| 2015/0254428 A1 | 9/2015 | Burkett | |
| 2016/0042148 A1 | 2/2016 | Bradley | |
| 2016/0321406 A1 | 11/2016 | Timmerman et al. | |
| 2017/0039331 A1 | 2/2017 | Bezdek et al. | |
| 2017/0161458 A1* | 6/2017 | Rourke | G06F 19/3456 |
| 2017/0255759 A1 | 9/2017 | McGrath | |
| 2017/0262594 A1 | 9/2017 | Janin et al. | |

OTHER PUBLICATIONS

NextGen:New Account Receivalbe Workflow, May 7, 2017, pp. 1-8 (Year: 2017).*

American Pharmacist Association (APhA): HIPPA; National Provider Identifier (NPI), Mar. 14-17, 2008, APhA 2008 SanDiego Annual Meeting Expositions, pp. 1-3. (Year: 2008).*

SEGIP: Now you can compare pharmacy prices for your prescriptions, Feb. 16, 2017, Management and Budget, State Employee Group Insurance Program, pp. 1-2. (Year: 2017).*

North Carolina Medicaid Management Information System (NCM-MIS): Howto Enter a Pharmacy Reversal on the Provider Portal;, Mar. 11, 2013, pp. 1-3. (Year: 2013).*

AccountingTools: Reversing entries, Nov. 9, 2017, pp. 1-2. (Year: 2017).*

Anderso, Brian N.: Are Your Pharmacy Benefits Being Adjudicated Properly? A PBM Audit Can Tell You, May 2014, Benefits Magazine, pp. 22-27. (Year: 2014).*

* cited by examiner

COMPUTER ARCHITECTURES AND ASSOCIATED METHODS FOR ENABLING REAL-TIME DATA DETERMINATIONS AND DISTRIBUTION

FIELD OF THE DISCLOSURE

The present disclosure generally relates to computer architectures and associated methods that use an internet protocol (IP) network and dynamically generate real-time data, provide system control, and provide an interactive graphical user interface for displaying the real-time data on a computing device.

BACKGROUND OF THE DISCLOSURE

Computing architectures that deliver real-time analysis may need to interface with multiple different electronic data sources. Such interfacing, however, can be challenging. Indeed, conventional architectures may not have the capability to interface with one or more different kinds of electronic data sources to provide actionable data for use in a real-time determination and representation. Moreover, translating data calls and data processes between such elements can be computationally complex and time-consuming. Conventional architectures may not have the capability to handle and integrate multiple different types of data from different sources, and may not be able to provide system control and the interactive display of such data.

The disclosed architectures and methods address at least these shortcomings. For example, the disclosed architectures and methods can provide accurate, real-time data determinations by handling multiple different data calls and interactions with disparate electronic data sources, and delivering determinations to interactive graphical user interfaces for display. The graphical user interface can further aggregate determinations to provide a composite display. By rapidly translating data calls from disparate systems and interfacing with such disparate systems, computing time and stress on computing systems may be reduced when generating real-time determinations.

SUMMARY

The improved computer architectures and associated methods described herein can permit or enable the distribution of real-time data.

According to one exemplary embodiment, a computer architecture for real-time data processing can be configured to receive, by a first server, a trial adjudication request for a cost determination. The trial adjudication request can include a request for an electronic calculation of a co-payment amount and a plurality of data sets obtained from a plurality of remote servers. The computer architecture can be configured to verify, by the first server, the trial adjudication request using a security protocol, wherein a password token of the trial adjudication request can be matched to a stored password token, and the stored password token can be variable. The computer architecture can be configured to transmit, by the first server, an adjudication command packet to a second server. The adjudication command packet can include at least one data set of the plurality of data sets and a command for a claim determination. The computer architecture can be configured to receive, by the first server, a response packet from the second server. The response packet can indicate a successful or failed claim determination performed by the second server and can include claim data generated by the second server. The computer architecture can be configured to determine, by the first server, that a successful claim determination was performed by the second server from the response packet, and transmit, by the first server, a reversal request packet to the second server. The reversal request packet can cancel the successful claim determination. The computer architecture can be configured to update, by the first server, a decentralized electronic ledger to reflect that the claim determination was successful, and perform, by the first server, the electronic calculation using the claim data generated by the second server, and generate a first result of the calculation. The computer architecture can be configured to transmit, by the first server, the first result to a third server configured to store the first result.

In accordance with this exemplary embodiment, the first result can be configured for display on a graphical user interface of a mobile computing device.

In accordance with this exemplary embodiment, the first result can be configured for display on a geographical map interface of the graphical user interface.

In accordance with this exemplary embodiment, the first result can be configured for display on a list interface of the graphical user interface.

In accordance with this exemplary embodiment, the computer architecture can be configured to receive, by the first server, a plurality of additional response packets that can indicate a successful or failed claim determination performed by a plurality of fourth servers and include claim data generated by the plurality of fourth servers. The computer architecture can be configured to determine, by the first server, that additional successful claim determinations were performed by at least some of the fourth servers from the plurality of additional response packets, and transmit, by the first server, additional reversal request packets to the fourth servers that performed the additional successful claim determinations. The additional reversal request packets can cancel the successful claim determinations of the fourth servers. The computer architecture can be configured to update, by the first server, the decentralized electronic ledger to reflect that the additional claim determinations were successful, and perform, by the first server, a plurality of electronic calculations using the claim data generated by the fourth servers, and generate a plurality of results of the calculations as second results. The computer architecture can be configured to transmit the second results to the third server.

In accordance with this exemplary embodiment, the second results can be configured for display on the graphical user interface of the mobile computing device along with the first result.

In accordance with this exemplary embodiment, the second results can be each different.

In accordance with this exemplary embodiment, the second results can be different to the first result.

In accordance with this exemplary embodiment, the plurality of data sets can include location data generated by a global positioning system.

In accordance with this exemplary embodiment, the plurality of data sets can include location data obtained due to an interaction with a graphical user interface of a mobile computing device.

In accordance with this exemplary embodiment, the password token of the trial adjudication request can be variable.

In accordance with this exemplary embodiment, the password token of the trial adjudication request and the stored password token can be varied on a periodic basis.

In accordance with this exemplary embodiment, the password token of the trial adjudication request and the stored password token can be varied on a non-periodic basis.

In accordance with this exemplary embodiment, the first result can be a co-payment amount.

In accordance with this exemplary embodiment, the adjudication command packet can comprise at least one masked data structure that can include one or a combination of bits reflecting a pharmacy identification number. The pharmacy identification number can identify a particular pharmacy.

In accordance with this another exemplary embodiment, a method for real-time data processing can comprise receiving, by a first server, a trial adjudication request for a cost determination. The trial adjudication request can include a request for an electronic calculation of a co-payment amount and a plurality of data sets obtained from a plurality of remote servers. The method can include verifying, by the first server, the trial adjudication request using a security protocol, wherein a password token of the trial adjudication request can be matched to a stored password token, and the stored password token can be variable. The method can include transmitting, by the first server, an adjudication command packet to a second server. The adjudication command packet can include at least one data set of the plurality of data sets and a command for a claim determination. The method can include receiving, by the first server, a response packet from the second server. The response packet can indicate a successful or failed claim determination performed by the second server and can include claim data generated by the second server. The method can include determining, by the first server, that a successful claim determination was performed by the second server from the response packet, and transmitting, by the first server, a reversal request packet to the second server. The reversal request packet can cancel the successful claim determination. The method can include updating, by the first server, a decentralized electronic ledger to reflect that the claim determination was successful, performing, by the first server, the electronic calculation using the claim data generated by the second server, and generating a first result of the calculation. The method can include transmitting, by the first server, the first result to a third server configured to store the first result.

In accordance with this exemplary embodiment, the first result can be configured for display on a graphical user interface of a mobile computing device.

In accordance with this exemplary embodiment, the first result can be configured for display on a geographical map interface of the graphical user interface.

In accordance with this exemplary embodiment, the first result can be configured for display on a list interface of the graphical user interface.

In accordance with this exemplary embodiment, the method can include receiving, by the first server, a plurality of additional response packets that can indicate a successful or failed claim determination performed by a plurality of fourth servers and can include claim data generated by the plurality of fourth servers. The method can include determining, by the first server, that additional successful claim determinations were performed by at least some of the fourth servers from the plurality of additional response packets, and transmitting, by the first server, additional reversal request packets to the fourth servers that performed the additional successful claim determination. The additional reversal request packets can cancel the successful claim determinations of the fourth servers. The method can include updating, by the first server, the decentralized electronic ledger to reflect that the additional claim determinations were successful, performing, by the first server, a plurality of electronic calculations using the claim data generated by the fourth servers, and generating a plurality of results of the calculations as second results. The method can include transmitting the second results to the third server.

DETAILED DESCRIPTION

The following describes embodiments of the present disclosure. The designs, figures, and description are non-limiting examples of embodiments of the present disclosure. Other embodiments may or may not include the features disclosed herein. Moreover, disclosed advantages and benefits may apply to only one or some embodiments, and should not be used to limit the scope of the present disclosure.

Medical insurance policies may cover only a portion of the price charged by a pharmacy for a prescription medication. The payment of the portion of the purchase price not covered by a patient's pharmacy benefits is called the "co-payment" or simply a "co-pay." The co-pay is the responsibility of the patient. Co-payments due from a patient seeking to purchase prescription medicine from a pharmacy can be quite high, and therefore may create a financial burden on the patient.

An insurance claim from a patient purchasing a prescribed medication is usually adjudicated by various Pharmacy Benefit Managers (PBMs). The present disclosure relates to an intermediary system that may be used to communicate these adjudications to the PBMs over a network connection. The PBM associated with the medical insurance company of the patient can be contacted over this network using the National Council for Prescription Drug Programs (NCPDP) standard protocol, for example.

Any adjudication made with one of the PBMs can be reversed post adjudication by embodiments of the present disclosure. This operation can require the identifier from the initial adjudication and an indication of the desire for reversal. After this operation, the PBM can cancel the claim against the individual's insurance.

A trial adjudication can include the submission of an adjudication request and the subsequent reversal of that request. Therefore, in a trial adjudication, for example, an adjudication request may be submitted to a PBM. The PBM can then adjudicate the request. Subsequently, the adjudication can be reversed. The adjudication prior to reversal can be used to determine how a PBM will handle a patient's insurance claim. For example, the adjudication can offer insight into the cost of a patient's co-pay for a particular PBM or a particular pharmacy.

Figure 1:
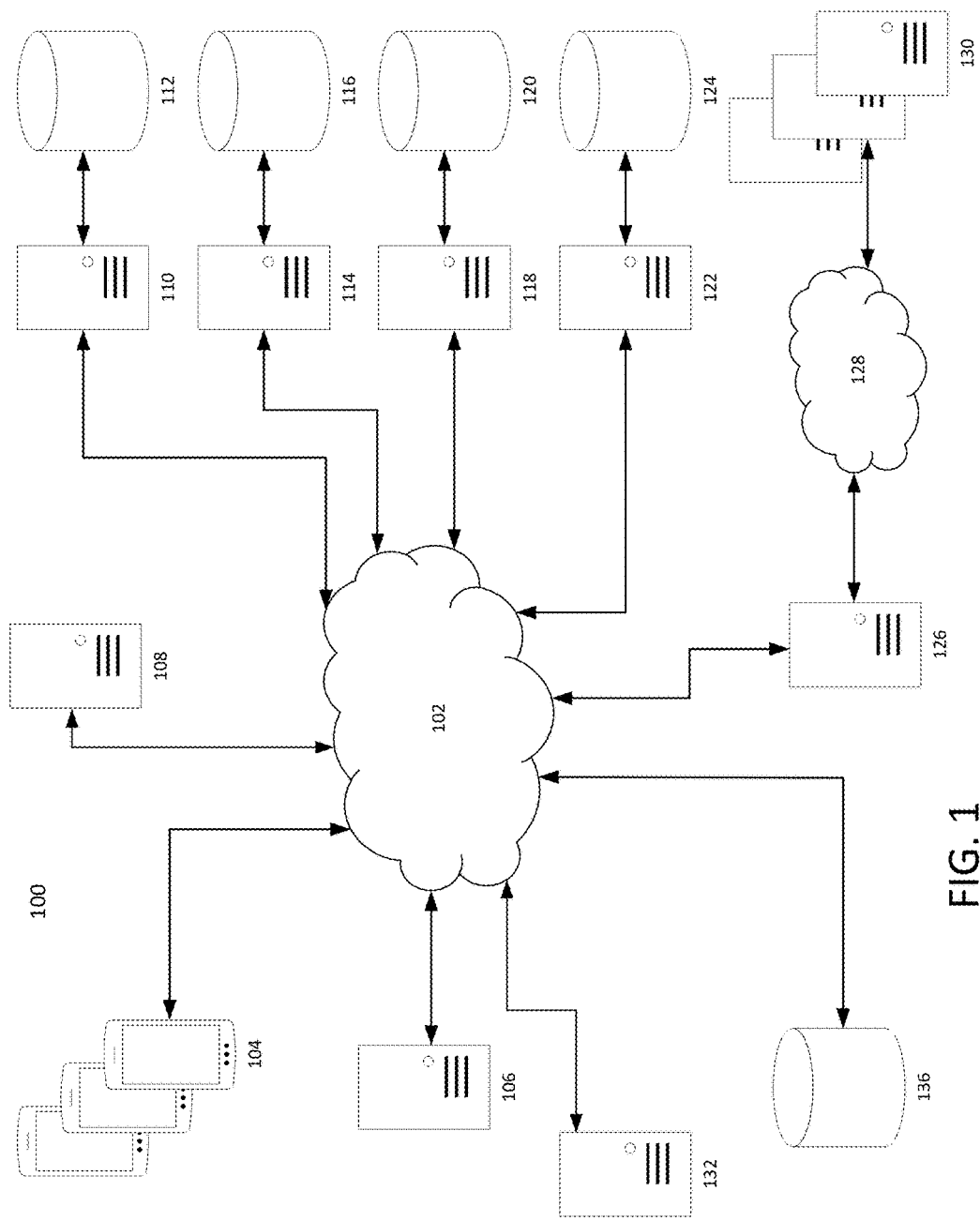
FIG. 1 shows an exemplary architecture t in accordance with embodiments of the present disclosure.

FIG. 1 shows an exemplary architecture 100 in accordance with embodiments of the present disclosure. It should be noted that the exemplary architecture of FIG. 1 is non-limiting, and one or more of the system elements may be combined into a single element, or split into one or more separate elements. Moreover, data calls and other transmissions of data that occur between the elements shown in FIG. 1 may occur serially, in parallel, or as a combination of serial and parallel operations.

Architecture 100 includes network 102. Network 102 can be a network that allows wireless, wired, or a combination of wireless and wired communication between architecture elements. For example, network 102 can be an internet protocol (IP) network. For example, network 102 can be a wireless network that uses cellular technology to allow communication between architecture elements. Network 102 can use a protocol such as WiFi, GSM/GPRS, or CDMA, for example. Network 102 can be a single network, or can comprise multiple networks. Network 102 can be used by each element of FIG. 1 for communication with each other. In some embodiments, one or more elements of FIG. 1 can bypass network 102 and instead communicate directly with each other, for example, via dedicated connections.

Architecture 100 includes at least one device 104 that interfaces with network 102. Device 104 can be a computing device. Device 104 can, for example, include a user interface. For example, the device 104 can include a graphical user interface (GUI) that allows a patient to enter insurance information and navigate co-pay resources. Device 104 can be, for example, a mobile device, a cellular phone, a mobile phone, a tablet device, a watch, a wrist-worn computing device, a laptop, a portable computer, a personal computer, a desktop computer, a programmable computer, a device with a speaker, a virtual reality (VR) device, a VR headset, a device that provides augmented reality display interfaces, or any other device capable of presenting information from a computer network, for example.

Device 104 can include location circuitry that determines a coordinate location of where a device 104 is located. For example, device 104 can include global positioning system (GPS) circuitry that allows for a location of device 104 to be determined. Device 104 can include a processor and a memory. The memory can have a software application stored in its memory. The processor can run the software application stored in the memory.

A operator of device 104 may want to know how much a particular prescription medicine will cost to him or her. The operator may use device 104, along with one or more of the elements in architecture 100, to determine this cost. For example, an operator of device 104 may scan their insurance card using camera and/or image processing capabilities of device 104 so device 104 obtains one or more of the operator's name data, insurance provider data, insurance identification number data, policy number data, and the like. The operator may alternatively enter such information into device 104 via an input device, such as a GUI keyboard of device 104, a keyboard, dialing pad, or the like. This information may be transmitted by device 104 via network 102 for storage in one or more of servers 106 and/or server 108, for example, and used by architecture 100 to determine the cost of one or more particular prescription medicines. Alternatively, this information may be stored locally in a memory of device 104.

FIG. 1 includes a number of servers (for example, servers 106, 108, 110, 114, 118, 122, 126, 130, and 132). One or more of these servers can be, for example, a server tower, laptop, portable computer, personal computer, desktop computer, programmable computer, or any other device capable of operating as a server. One or more of these servers can be remote servers, for example.

FIG. 1 includes a number of databases (for example, databases 112, 116, 120, 124, and 136). One or more of these databases can be, for example, a server tower, laptop, portable computer, personal computer, desktop computer, programmable computer, or any other device capable of operating as a database.

It should be noted that one or more of servers 106, 108, 110, 114, 118, 122, 126, 130, and 132 and their associated databases (for example, databases 112, 116, 120, 124, and 136) may be disparate computing systems that structure their data differently. Therefore, interactions involving these elements may require data translations so these elements can interface with each other. These translations can allow the elements of architecture 100 to communication with each other quickly, and advance the computing speed and capabilities of computerized co-payment determination systems.

Server 106 can be a managing server, and can be responsible for handling data transmitted from device 104, and thereby managing user interactions with architecture 100 input via device 104. For example, server 106 can translate data calls. Data calls from device 104 can include, for example, data regarding identification and quantity information about a certain prescription medication, data regarding a medication prescriber, and data regarding a user's insurance plan. Data calls from device 104 can also include location data. The location data can be GPS coordinate data that is generated by device 104 and indicates a current, past, or future location of device 104. Location data can be data that reflects a map location selected by a user of device 104. For example, location data can reflect dropped pin data of a certain location selected or input by a user via a GUI of device 104, or can reflect a cross road selected by a user of device 104.

Server 108 can be a data lookup server, and can receive data from server 106 that reflects medical and/or insurance and/or location information from device 104. Server 108 can store the received data. Server 108 can use one or more of the received data from server 106 to request derived data from one or more of a number of different data servers, such as server 110, server 114, server 118, and server 122. These requests may be made serially in any order to each of servers 110, 114, 118, 122, or may be sent in parallel to each of servers 110, 114, 118, 122 at the same or substantially the same time. Derived data can include, for example, data from servers in response to data calls. This derived data can be used by architecture 100 to provide a user with real-time co-pay information about the copy of a prescription medication from different pharmacies for display in real-time via an interactive GUI of device 104. Real-time can be an amount of time, such as a number of milliseconds, that the processing of architecture 100 takes such that co-payment information is displayed on the interactive GUI of device 104 substantially immediately. It should be noted that in some embodiments, server 108 may alternatively receive data generated by device 104 directly from device 104, without handling by server 106.

Server 110 can be a pharmacy data server 110, and can receive a derived data request from server 108. Server 110 can verify the derived data request to make sure it is a valid request. The verification can be performed according to a security protocol associated with server 110. For example, server 110 can use a variable security protocol to verify that the derived data request includes an encrypted password token that is recognizable to server 110. If the password token of the request matches that of server 110, the request can be deemed valid. The password token can change periodically, and can be updated at both server 110 and server 108 (or device 104). For example, the password token can change periodically after a certain number of days, hours, minutes, or seconds, or non-periodically after a certain number of days, hours, minutes, or seconds. It should be noted that servers 110, 114, 118, 122, 126, and 132 may perform similar or substantially the same kind verification to ensure that derived data requests that they receive are valid.

If the received request is a valid request, server 110 can communicate with pharmacy database 112 to obtain pharmacy information stored in pharmacy database 112. The pharmacy information can include location information, opening hours, and medication stock, for example, about one or more pharmacies that are within a certain distance from the location reflected by the location data received from device 104. The pharmacy information can include information regarding a store name of the pharmacies, whether the pharmacy is part of a pharmacy chain of stores, and whether the pharmacy is part of a network that negotiates certain prices. The request received from server 108 can specify a certain chain, location, and/or opening hours of a pharmacy as specified by device 104. Server 110 can return the obtained pharmacy information that was requested by the derived data request to server 108.

As noted above, pharmacy database 112 can store data about pharmacies. For example, pharmacy database 112 can store location information, opening hours, and medication stock, for example, about one or more pharmacies. The location information about the one or more pharmacies can include, for example, GPS coordinate location data, or other kinds of geo-location data.

Server 114 can be a prescriber data server, and can receive a derived data request from server 108. Server 114 can verify the derived data request to make sure it is a valid request. If it is a valid request, server 114 can communicate with prescriber database 116 to obtain data regarding authorized prescribers. Such prescribers can be, for example, physicians, physician assistants, or nurses. The obtained data can include data that reflects a national provider identifier (NPI), for example, of a prescriber. Server 114 can return the obtained data regarding authorized prescribers that was requested by the derived data request to server 108.

Server 114 can compare the data of the derived data request with the data obtained from prescriber database 116 to determine if the prescriber information included in the data from device 104 is correct and/or verified. For example, server 114 can compare NPI data included in a call from device 104 and indicated by the derived data request with the data obtained from prescriber database 116. If the NPI of the call from device 104 does not match with NPI data of the data obtained from prescriber database 116, a message can be broadcast to server 106 (or directly to device 104) that indicates a user's request cannot be processed. Server 106 can perform data transformations of the message, if needed, so device 104 can properly process it, and send the message to device 104. Device 104 can then display in real-time via its GUI that the user's request could not be processed.

Prescriber database 116 can contain data regarding individuals who are authorized prescribers and able to write prescriptions. Such data can be NPI data, for example, that identifies a national provider identifier of an individual. Prescriber database 116 can also contain any other relevant identifiers of individuals who can write prescriptions, such as office locations, medical specialties, education information, and medical experience, for example.

Server 118 can be a medication data server, and can receive a derived data request from server 108. Server 118 can verify the derived data request to confirm it is a valid request. If it is a valid request, server 118 can communicate with medication database 120 to obtain data regarding a certain medication. This data can, for example, include identification data for a particular medication, and data that reflects alternatives to the particular medication, such as generic versions or other brands that have the same/similar efficacy for treating an illness. Server 118 can return the obtained data regarding a certain medication that was requested by the derived data request to server 108.

Medication database 120 can contain data regarding medications. As noted above, this data can, for example, include identification data for a particular medication, and data that reflects alternatives to the particular medication, such as generic versions or other brands that have the same/similar efficacy for treating an illness. Medication database 120 can also contain data regarding one or more drugs which can be prescribed along with possible quantities, packaging, identification numbers and equivalent medication, such as generic versions or other brands that have the same/similar efficacy for treating an illness.

Data server 122 can be a processor control number (PCN) data server, and can receive a derived data request from server 108. Server 122 can verify the derived data request to make sure it is a valid request. If it is a valid request, server 122 can obtain a PCN data from BIN database 124 that relates to the insurance plan information included in a data call from device 104. A PCN is an identifier for a pharmacy transaction, and can be assigned to a particular pharmacy benefit manager (PBM) for internal routing. The PCN data can be used to determine how a PBM handles a user's prescription claim, and determine an amount of the user's co-pay for particular medications. For example, PCN data can be utilized by a PBM to adjudicate a claim. PCN data can be included in a claim submitted to a PBM. Server 122 can return the obtained PCN data that was requested by the derived data request from server 108. In some embodiments of the present disclosure, one or more PBMs may not use a PCN. In such a case, for example, server 122 may not return PCN data as a result of a derived data request from server 108. Here, server 122 may not return anything to server 108, or may return a data message that indicates one or more PBMs do not use a PCN.

After receiving the derived data request from server 108, server 122 can also validate eligibility of the patient requesting a prescription and making a claim to a PBM. If the eligibility is validated, server 108 may make one or more requests to server 122, in parallel, requesting PCN data for one or more other medication claims. If any of the one or more other claims are returned as invalid by server 122, then all of the one or more claims may be canceled.

Bank identification number (BIN) database 124 can contain BIN data and corresponding PCN data. The PCN data relates to insurance plan information. BIN data reflects which PBM should receive a claim for a prescription.

Server 110, server 114, prescriber database 116, server 118, and server 122 can communicate with databases 112, 116, 120, and 124, respectively, via a wireless, wired, or a combination of wireless and wired connection. The communication can be, for example, via network 102, but for ease of viewing, these elements are not shown as communicating with each other via network 102 in FIG. 1. Alternatively, the communication can be via direct communications that do not include network 102.

In some embodiments, device 104 and/or server 108 can send derived data requests directly to each of servers 110, 114, 118, and/or 122, and then direct one or more of servers 110, 114, 118, and/or 122 to send their data directly to server 126. Server 126 can then interact with PBM servers 130 as noted above.

As discussed above, server 108 can use one or more of the received data from server 106 (or device 104) to request derived data from one or more of a number of different data servers, such as server 110, server 114, server 118, and server 122. These requests may be made serially in any order, or may be made in parallel. Moreover, if a request to one server fails or otherwise does not result in return of requested data, server 108 (or device 104) may cancel the cost request made by device 104. Server 108 can communicate with server 106 to indicate that the request failed. Device 104 may thereafter display via its GUI that the cost request could not be completed.

In addition to the tasks described above, server 108 can also process the obtained pharmacy information data, data regarding authorized prescribers, data regarding a certain medication that was requested, and PCN data from each of server 110, server 114, server 118, and server 122. Server 108 can then perform its own verification process using the obtained data to ensure that one or more requests from device 104 are proper. Once server 108 determines that the request from device 104 is proper, server 108 can communicate with server 106 and can indicate that a request from device 104 was proper. Server 108 can then communicate with server 126 and request adjudication of a particular co-pay trial.

Server 126 can be an adjudication server, and can receive the adjudication request from server 108. Server 126 can verify the request from server 108 and thereafter communicate with one or more PBM servers 130 via intermediary network 128 to retrieve co-pay information for a particular medication requested by device 104, as well as confirm one or more PCN numbers. The adjudication server 126 can provide insurance information of a patient (provided to architecture 100 via device 104, for example), as well as demographic data regarding the patient (provided to architecture 100 via device 104, for example), to the one or more PBM servers so that co-pay information can be determined, using this information, by the one or more PBM servers. Server 126 can also provide the data obtained from one or more of servers 110, 114, 118, and/or 122 to one or more of the PBM servers, and the one or more PBM servers can use this data (alone or in combination with one or more of the insurance and demographic data) to determine co-pay information. Communication over intermediary network 128 can be performed using a National Council for Prescription Drug Programs (NCPDP) protocol, for example. It should be noted that device 104 may communication directly with server 126 via network 102, and server 126 may perform the processes described above with respect to servers 106 and 108.

Intermediary network 128 can be a wired, wireless, or combination of wired and wireless networks as described with regard to network 102. Intermediary network 128, can alternatively be part of network 102. For example, when intermediary network 128 is part of network 102, servers 130 are directly connected to network 102. Intermediary network 128 can include switch functionality that routes data from one architecture element to another.

Pharmacy benefit manager (PBM) servers 130 can contain information regarding pharmacy benefit managers. According to embodiments, each of the PBM servers 130 can correspond to a different PBM. PBMs can administer drug benefit programs for health insurance plans, and can process and pay prescription medication claims. One or more PBM servers 130 are accessed by adjudication server 126 to determine the amount of money that a PBM will pay toward a prescription medication indicated by a user of device 104. A user's co-pay for that medication can thereafter be determined by server 126 by subtracting the amount of money that the PBM will pay from the medication's price. Since one or more PBM servers 130 can be accessed to determine how much each PBM will pay toward a prescription medication, one or more co-pays can be determined. The determinations may be trial adjudications performed by server 126. During each trial adjudication, server 126 may instruct one or more of the PBM servers 130 to initiate a claim for a prescription medicine so the amount of money that each PBM will pay toward the prescription can be determined. Adjudication server 126 may then cancel the claim so it is not fully processed to completion. Each determined co-pay can be communicated to response database 136.

Response database 136 can store each determined co-pay from each PBM server 130. Response database 136 can translate the determined co-pay into data that is readable by device 104, and displayable by a GUI of device 104.

Server 132 can be a response lookup server, and can communicate with response database 136 to parse the various determined co-pays and determine co-pays that relate to device 104's request to server 106. Server 132 can then relay the determined co-pays to server 106. Server 106 can communicate with device 104 and transmit the determined co-pays to it.

Device 104 can display the determined co-pays on a GUI of the device. The determined co-pays can be displayed as a list of co-pay prices, or on a map that indicates the location of each pharmacy offering the medication and the co-pay associated with each pharmacy. The display may be made in real time. Moreover, the displays may be continually refreshed so that prices change if trial adjudications result in revised prices. The display of co-pays on device 104 is further discussed with reference to FIG. 4.

In some embodiments of the present disclosure, one or more PBM servers 130 can be accessed without reference to the data of one or more of servers 110, 114, 118, and/or 122. For example, server 108 may not send a derived data request to one or more of servers 110, 114, 118, and/or 122, or may send such a request but not receive data in return. In some embodiments, server 108 can send a derived data request to one or more of servers 110, 114, 118, and/or 122, but may not receive any response in return. In such embodiments, for example, one or more PBM servers 130 can still be accessed by server 126 to determine the amount of money that a PBM will pay toward a prescription medication indicated by a user of device 104. The determination, however, will not contemplate the data that was not returned from one or more of servers 110, 114, 118, and/or 122.

Figure 2:
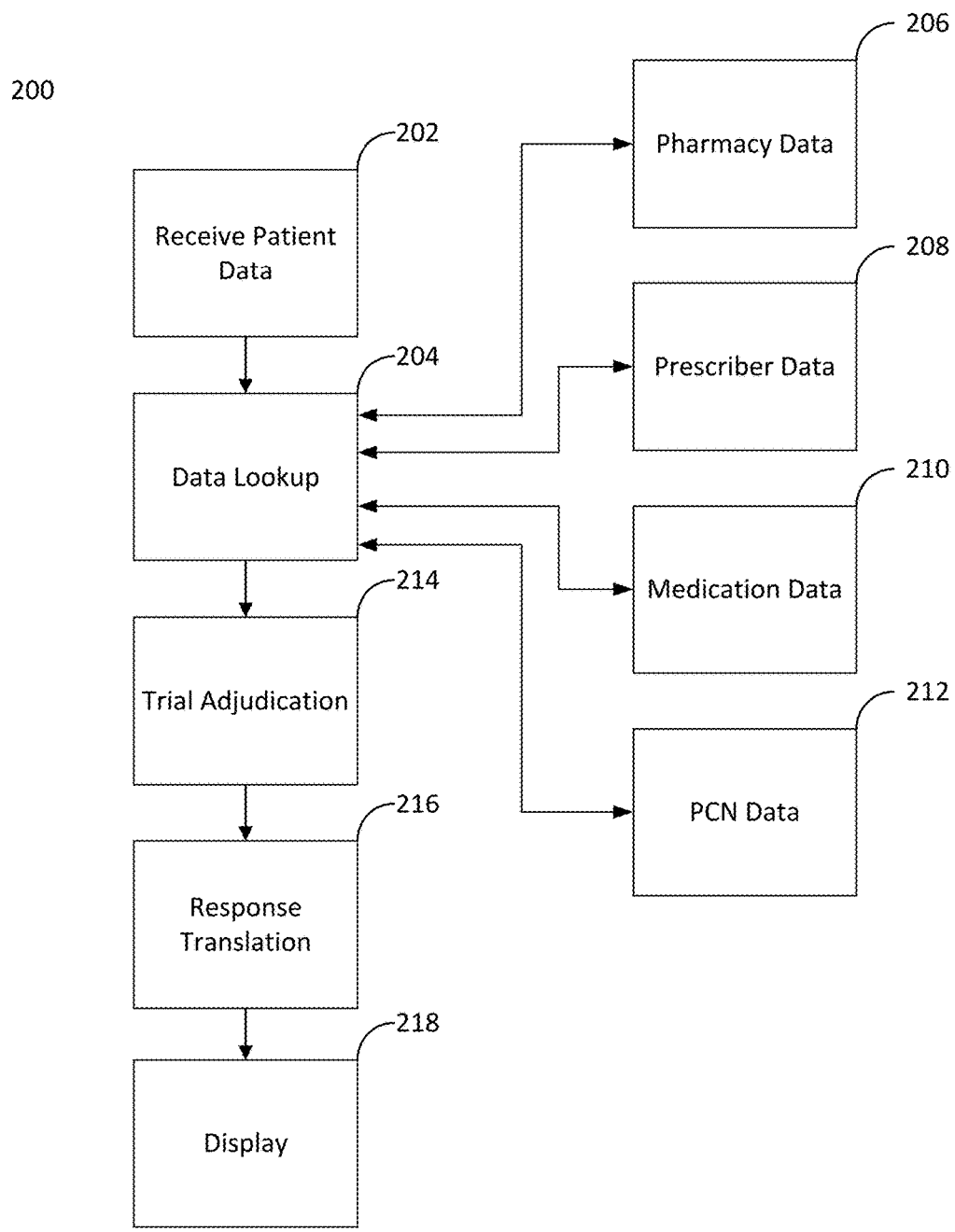
FIG. 2 shows an exemplary process for in accordance with embodiments of the present disclosure.

FIG. 2 shows an exemplary process 200 for retrieving prescription benefit information in accordance with embodiments of the present disclosure. Architecture 100 of FIG. 1, for example, can be used to perform process 200.

At step 202, process 200 receives patient data. This data can come from a variety of different sources, such as a device 104. Device 104 can be, for example, a patient's device, a medical professional or healthcare practitioner's device or an electronic medical record system. Patient data can be data regarding a patient's prescription, and can also include insurance information. For example, patient data can be sent via data calls from device 104. The data calls can include data regarding identification and quantity information about a certain prescription medication, data regarding a medication prescriber, and data regarding a user's insurance plan. The data calls can also include location data. The location data can be GPS coordinate data that is generated by device 104 and indicates a current or past location of device 104. Location data can be data that reflects a map location selected by a user of device 104. For example, location data can reflect dropped pin data of a certain location selected or input by a user via a GUI of device 104, or can reflect a cross road selected by a user of device 104.

The patient data of step 202 can be transmitted to a data look up system for processing at step 204. The data lookup system can be, for example, server 108. The data lookup system can, for example, store the data in a way which is compatible with United States data privacy laws. The data lookup system can make a call to one or more data sources using steps 206, 208, 210, and 212.

At step 206, process 200 can send a request for derived data to a pharmacy data server, such as server 110. The pharmacy data server can verify the derived data request to make sure it is a valid request. If it is a valid request, the pharmacy data server can communicate with a database such as pharmacy database 112 to obtain pharmacy information stored in the database. The pharmacy information can be data that reflects, for example, location information, opening hours, and medication stock about one or more pharmacies that are within a certain distance from the location reflected by location data of the received patient data. The pharmacy information can include, for example, information regarding a pharmacy store name, whether the pharmacy is part of a pharmacy chain of stores, and whether the pharmacy is part of a network that negotiates certain prices. The request received from the data lookup system can specify a certain chain, location, and/or opening hours of a pharmacy as specified by the patient data. The pharmacy information can also include data that corresponds to an NPI of a medical professional or healthcare provider. The pharmacy data server can return the obtained pharmacy information that was requested by the derived data request to the data lookup system.

At step 208, the data lookup system can send a request for derived data to a prescriber data server, such as server 114. The prescriber data server can verify the derived data request to make sure it is a valid request. If it is a valid request, the prescriber data server can communicate with a prescriber database to obtain data regarding authorized prescribers. Such prescribers can be, for example, physicians, physician assistants, or nurses. The obtained data can include data that reflects a national provider identifier (NPI) and/or a Drug Enforcement Administration ("DEA") number, for example, of a prescriber. Data can be converted into the NPI and/or DEA number format, for example. The DEA number can be an identifier assigned to a health care provider by the Drug Enforcement Administration, and identifies that the provider is allowed to write prescriptions for certain medications and/or substances. Prescriber data server can return the obtained data regarding authorized prescribers that was requested by the derived data request to data lookup system.

Prescriber data server can compare data of the derived data request with the data obtained from the prescriber database to determine if prescriber information included in data from a device is correct and/or verified. For example, prescriber data server can compare NPI data included in a call from the device and indicated by the derived data request with the data obtained from prescriber database. If the NPI does not match with NPI data of the data obtained from prescriber database, a message can be broadcast to a managing server that indicates a user's request cannot be processed. The managing server can perform data transformations of the message (if needed) so the device can properly process it, and send the message to the device. The device can then display in real-time via its GUI that the user's request could not be processed.

At step 210, process 200 can send a request to a medication data source, such as server 118, for example. Medication data source can verify the derived data request to make sure it is a valid request. If it is a valid request, medication data source can communicate with a medication database to obtain data regarding a certain medication. This data can, for example, include identification data for a particular medication, and data that reflects alternatives to the particular medication, such as generic versions or other brands that have the same/similar efficacy for treating an illness. The medication data server can return the obtained data regarding a certain medication that was requested by the derived data request to data lookup system.

Before sending the obtained data regarding a certain medication to the data lookup system, the medication data source can convert data into a set of National Drug Codes (NDCs), which are specified as part of the NCPDP standard. In order to get the correct NDCs, the medication data source can provide checks for validity against existing prescription standards. This can include but is not limited to quantity, strength, form, packaging as well as other attributes which can impact the final dispensed medication.

Figure 5:
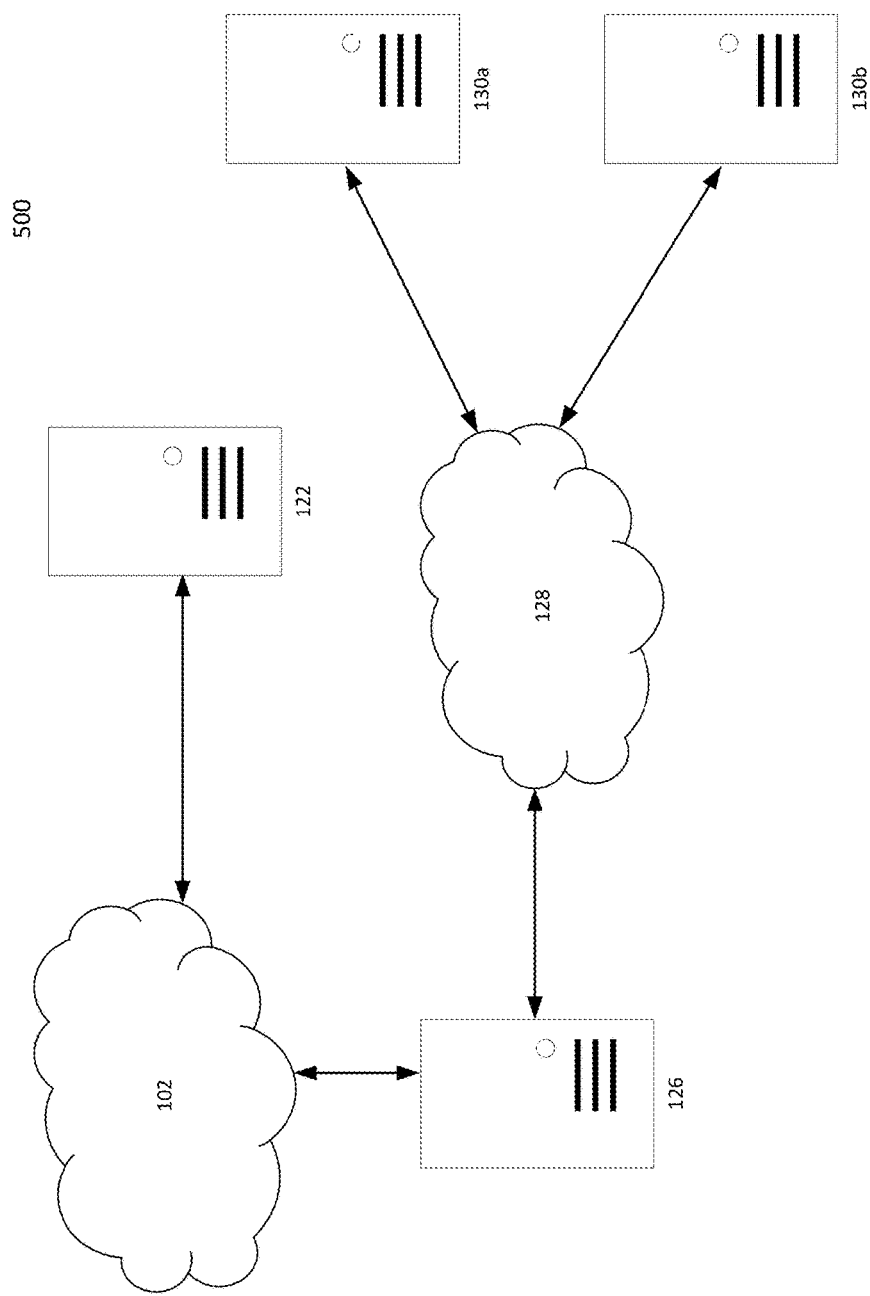
FIG. 5 shows an exemplary PCN lookup system in accordance with embodiments of the present disclosure.

At step 212, process 200 can send a request to a PCN data source, such as server 122. The PCN data source can verify the derived data request to make sure it is a valid request. If it is a valid request, the PCN data source can obtain a PCN data from a BIN database that relates to the insurance plan information included in a data call from the device. PCN data source can return the obtained PCN data that was requested by the derived data request to the data lookup system. The PCN data source can include a PCN lookup mechanism that takes patient data of step 100 included in the request to the PCN data source, and finds a PCN number applicable to the patient's insurance. The details of how the PCN lookup can operate are shown in FIG. 5.

As noted above, one or more of steps 206, 208, 210, and 212 may not be performed in process 200. Alternatively, all of steps 206, 208, 210, and 212 can be performed by process 200.

After data is received by the data lookup system of step 204 as a result of steps one or more of steps 206, 208, 210, and 212, this data can be processed at step 204. A verification process using the obtained data can also be performed to ensure that the request from the device is proper. Once data lookup system determines that the request was proper, the system communicates with a managing server and indicates that the request was proper. The process then can continue to trial adjudication at step 214.

At step 214, trial adjudication can be performed by an adjudication server such as server 126. The adjudication server can receive the adjudication request. The adjudication server can verify the request and thereafter communicate with one or more PBM servers to retrieve co-pay information for a particular medication requested, as well as confirm one or more PCN numbers. The adjudication server can provide insurance information of a patent to the one or more PBM servers so that co-pay information can be determined, using this information, by the one or more PBM servers. Communication by the adjudication server can be performed using a National Council for Prescription Drug Programs (NCPDP) protocol, for example.

Figure 3:
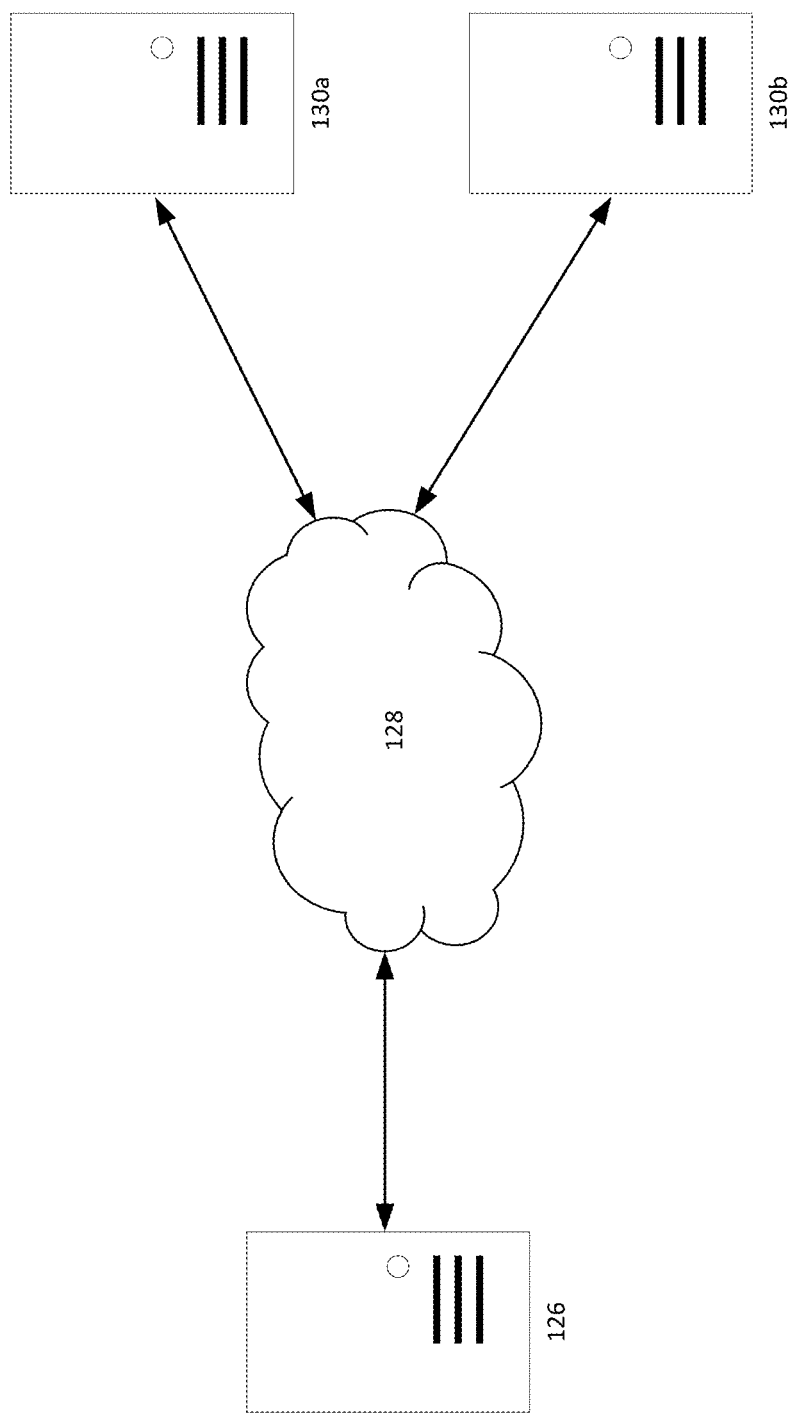
FIG. 3 shows an exemplary architecture for trial adjudication of a patient claim in accordance with embodiments of the present disclosure.

One or more PBM servers can be accessed by adjudication server to determine the amount of money that a PBM will pay toward a prescription medication indicated by a user of the device in the patient data. A user's co-pay for that medication can thereafter be determined by subtracting the amount of money that the PBM will pay from the medication's price. Since one or more PBM servers can be accessed to determine how much each PBM will pay toward a prescription medication, one or more co-pays can be determined. The details of how the trial adjudication works is shown in FIG. 3 and its accompanying description. Each determined co-pay can be communicated from the adjudication server to a response database at step 216.

Figure 6:
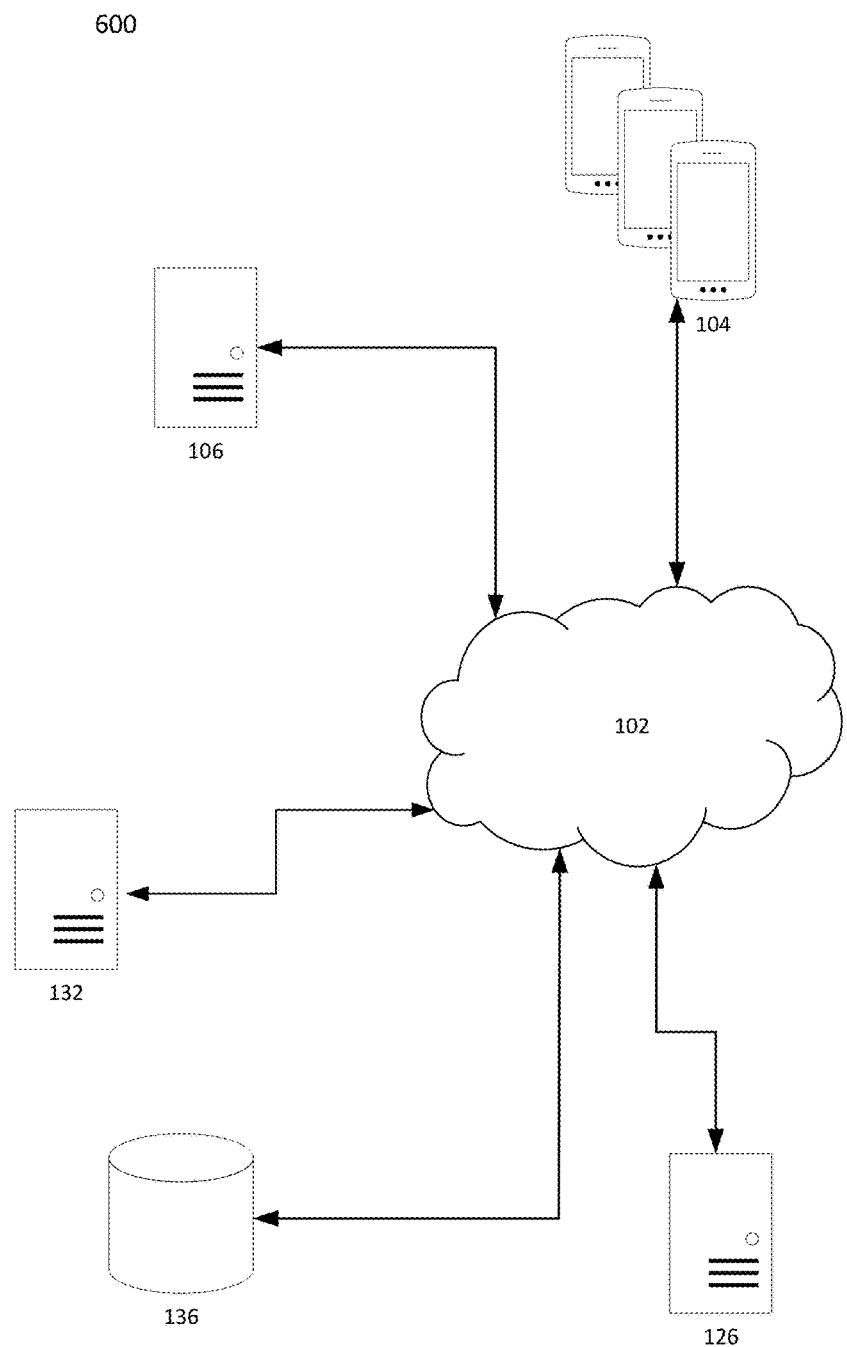
FIG. 6 shows an exemplary system that can translate PBM responses to patient understandable information in accordance with embodiments of the present disclosure.

At step 216, a response database can store each determined co-pay. The response database can translate the determined co-pay into data that is readable by the device that sent the patent data, and displayable by a GUI of the device. Details of how the response translation system works are shown in FIG. 6 and its accompanying description.

At step 218, the process 200 can display the determined co-pays on a device, for example, using a GUI. The device can be controlled to display particular co-pays. The determined co-pays can be displayed as a list of co-pay prices, or on a map that indicates the location of each pharmacy offering the medication and the co-pay associated with each pharmacy. The display of co-pays on the device is further discussed with reference to FIG. 4.

FIG. 3 shows an exemplary architecture for trial adjudication using server 126, intermediary network 128, and one or more PBM servers 130 (for example, 130*a* and 130*b*) of FIG. 1, in accordance with some embodiments of the present disclosure. The trial adjudication can take place in step 214 of FIG. 2, for example. The trial adjudication architecture can be used to determine a co-payment cost in real-time for a patient using a wide variety of different data types. For example, a current patient co-payment amount, treatment information (e.g. step therapy), reasons why the patient cannot obtain co-payment information, the patient pay amount (which could be different from the co-payment), as well as other details about the medication and treatment approach can be used to determine a co-payment in real-time.

Server 126 runs a server process to determine an adjudication. As noted above, server 126 can receive the adjudication request from a managing server, such as server 106. Server 126 can verify the request and thereafter communicate with PBM server 130*a* and/or 130*b* via intermediary network 128 to retrieve co-pay information for a particular medication requested by device 104, as well as confirm one or more PCN numbers. Communication over intermediary network 128 can be performed using a National Council for Prescription Drug Programs (NCPDP) protocol, for example.

For example, server 126 can receive data obtained by a management server 106 that reflects the data obtained by server 108. The data can be received by server 126 from each of the data sources in architecture 100 (e.g., each of servers 110, 114, 118, and/or 122), or can be received as a combined data package from server 106 or server 108. The data may be structured as a respective set of data, where each set corresponds from one of servers 110, 114, 118, and/or 122 that it originated from. A data package may include one or more of these sets of data. The data received by server 126 may be included with the adjudication request. Moreover, server 126 may verify the request using a variable security protocol. The variable security protocol may be the same or substantially the same as that previously described with respect to server 110, for example. Server 126 can send some or all of the received data over intermediary network 128 to PBM server 130*a* or 130*b* as an adjudication command packet.

The adjudication command packet can include one or more masked data structures. A masked data structure can include one or a combination of identification bits that reflect one or more particular pharmacy identification numbers. Alternatively, or in addition, the masked data structure can include one or a combination of bits that reflect one or more particular NPI numbers. The masked data structures can be used to command one or more of PBM servers 130*a* or 130*b* to provide one or more different claim responses that correspond to the one or more pharmacies. The one or more pharmacies can be identified by the identification bit(s) and/or one or more NPI numbers. The one or more of PBM servers 130*a* or 130*b* can verify that the masked data structures refer to a particular pharmacy by processing the identification bits and/or NPI numbers, and using a security protocol. For example, the variable security protocol previously discussed can be used. For example, a masked data structure can include a single identification bit or combination of identification bits that refers to a single pharmacy identification number (and therefore a single pharmacy). The masked data structure can be included in adjudication command packet and used by server 130*a* and/or 130*b* to return one or more claim responses that correspond to that pharmacy. Server 130*a* and/or 130*b* can recognize the single identification bit or combination of identification bits, and determine that the request is in regard to the single pharmacy. In another example, multiple masked data structures can be included in an adjudication command packet. Each masked data structure can include a single identification bit or combination of identification bits that refer to a respective pharmacy. Server 130*a* and/or 130*b* can recognize the single identification bit or combination of identification bits of each masked data structure, and determine that the request is in regard to multiple pharmacies reflected by the multiple masked data structures. Server 130*a* and/or 130*b* can output one or more claim responses that correspond to each of the multiple pharmacies. These examples therefore show how servers 130*a* and/or 130*b* can each output a single claim response for a single pharmacy, or multiple responses for multiple pharmacies. The responses can be different for different pharmacies, which can mean that co-payment determinations can be different for different pharmacies.

In another example, as noted above, the adjudication command packet can include one or more masked data structures that reflect one or more NPI numbers. The one or more NPI numbers can reflect one or more pharmacies. The adjudication command packet can be sent to one or more of PBM servers 130*a* and 130*b*. The PBM server(s) that receives the adjudication command packet can decode the one or more NPI numbers and provide a claim response(s) that is specific to each pharmacy indicated by the one or more NPI numbers. Thus, PBM server(s) can provide co-payment information for the one or more pharmacies that are reflected by the one or more NPI numbers of the one or more masked data structures of the adjudication command packet. Co-payments for a patient can thereafter be determined for a user at each of these pharmacies by adjudication server 126. It should be noted that a pharmacy need not be the entity sending an adjudication command packet to the one or more PBM servers. Instead, the masked data structures of the adjudication command packet can pose a pharmacy, and PBM servers receiving the adjudication command packet act as if they are receiving and processing a claim request from a pharmacy.

The data can be sent in NCPDP format servers 130a and 130b. Intermediary network 128 can route the data to the correct one or more PBM servers 130a and 130b using BIN information. For example, intermediary network 128 can call one or more of PBM servers 130 and route the data to it. A PBM server 130 can process the data and respond with a claim response. The claim response can identify whether the claim was successful or a failure. A successful claim indicates that a co-payment can be determined by the PBM server 130. A failure claim indicates that a co-payment could not be determined by the PBM server 130. The response is transmitted by PBM server 130 via intermediary network 128 to server 126. The response data can be structured as a response data packet. One or more responses can be obtained from one or more PBM servers at the same time or at different times. The responses can be provided fast enough such that they are eventually delivered to a user's device in real time.

Server 126 can transmit the response data to a response database 136 (shown in FIG. 1, not shown in FIG. 3). Response database 136 can store each determined co-pay from each PBM server 130. Response database 136 can translate the determined co-pay into data that is readable by device 104, and displayable by a GUI of device 104. This will allow the architecture to inform the patient of all co-pay options, and allow the patient to determine their best available option.

Server 126 can make another call which would proceed in a similar manner as described above for FIG. 3. In the case the request was successfully adjudicated with one of PBM servers 130, server 126 can submit an electronic reversal request packet to be processed by the same PBM server 130. This will mean there is no outstanding claim at this PBM server. In case of failure, a ledger system can be used to reconcile successful versus failed claims and alert any reconciliation issues. The ledger system can be decentralized, meaning that it can be stored in multiple elements of system 100. The ledger system may be continually updated by the multiple elements of architecture 100, and may therefore be verified by the multiple elements to ensure accuracy.

Figure 4:
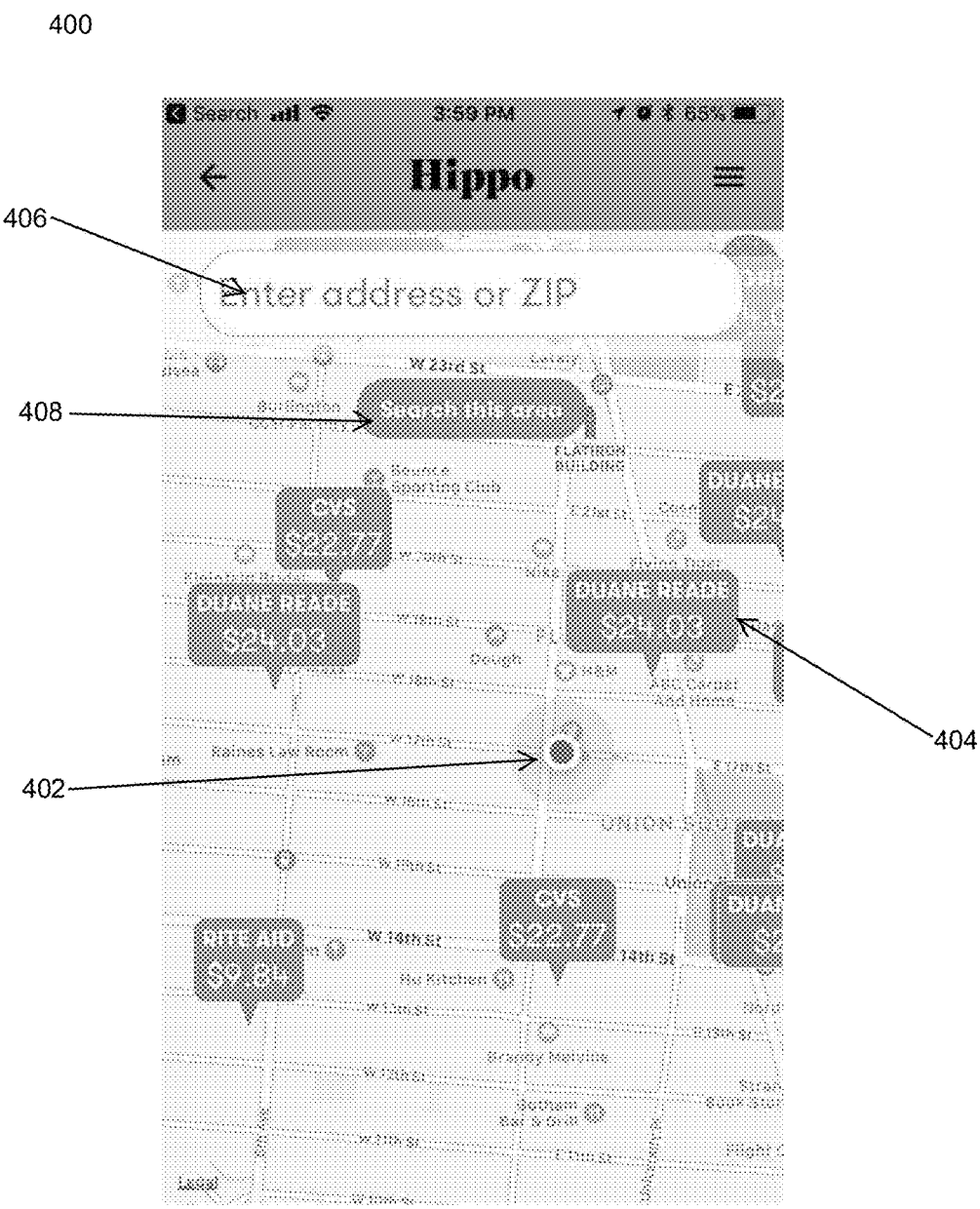
FIG. 4 shows an exemplary visual representation of co-pay prices including pharmacy location in accordance with embodiments of the present disclosure.

FIG. 4 shows an exemplary visual representation 400 of co-pay prices including pharmacy location in accordance with embodiments of the present disclosure. This is one example of a possible way to show pharmacy prescription information in a geographic format on a computing device, such as device 104. An alternative display could be a tabular or listed format, for example. For example, a device 104 can display a map by utilizing the geo-location of the device reflected by item 402. A user can enter their address details explicitly in region 406, if desired. For example, a user can want to enter address details in region 406 if geolocation of device 104 is not available. The representation of address could take a number of different forms, such as a ZIP code, full or partial address, or exact geo-location, for example. If it can be determined, the patient's current location 402 will be shown on the map. All pharmacies visible in the map scope will be displayed via a pharmacy icon 404. The pharmacy icons 404 can list a prescription co-pay, for example. Icons 404 can animate, for example, by changing different colors, changing shape, or changing in size. Animations of icons 404 may be based on data about a co-payment received from server 106 via network 102 of architecture 100, for example. Item 408 can be an icon that a user can interact with using the graphical user interface. For example, if a user selects icon 408, co-payment determinations using architecture 100 can be provided for pharmacies located in a geographic area displayed by the interface. A user can select icon 408 by interacting with a touch screen or using a cursor, for example. A user can scroll across the displayed geographic area by interacting with a touch screen or using a cursor, for example, to adjust the displayed geographic area and display a different geographic area. A user can zoom in or zoom out to adjust the displayed geographic area by interacting with the touch screen or using a cursor, for example.

The visual representation 400 of FIG. 4 can provide a graphical user interface that displays aggregated data as a composite display. For example, the interface can aggregate one or more determinations made in real-time regarding co-payment information into a composite interactive interface, and display the aggregated real-time determinations. The aggregated determinations can control what and how the interface displays.

FIG. 5 shows an exemplary architecture 500 for PCN lookup in accordance with embodiments of the present disclosure. The PCN can be a secondary routing identifier assigned by the PBM for its own internal routing needs. Not all PBMs can use PCNs, but those that do can require that the PCN be submitted along with a claim in order for the claim to adjudicate. FIG. 5 shows an exemplary trial adjudication with PCN lookup that can be performed using server 126, intermediary network 128, and one or more PBM servers 130 (for example, 130a and 130b) of FIG. 1, in accordance with some embodiments of the present disclosure. Moreover, FIG. 5 includes network 102 and server 122.

In FIG. 5, server 126 can perform an adjudication that includes a PCN lookup. As noted above, server 126 can run a server process to determine an adjudication. As noted above, server 126 can receive the adjudication request from a managing server, such as server 106. Server 126 can verify the request and thereafter communicate with PBM server 130a and/or 130b via intermediary network 128 to retrieve co-pay information for a particular medication requested by device 104, as well as confirm one or more PCN numbers. Communication over intermediary network 128 can be performed using a National Council for Prescription Drug Programs (NCPDP) protocol, for example.

For example, server 126 can receive data obtained by a management server 106 that reflects the data obtained by server 108. The data can be received by server 126 from each of the data sources in architecture 100 (e.g., each of servers 110, 114, 118, and/or 122), or can be received as a combined data package from server 106 or server 108. Server 126 can send its received data over intermediary network 128 to PBM server 130a or 130b.

When a PCN lookup is performed by server 126, the server can communicate with server 122 via network 102 or directly via dedicated communication. In FIG. 5, communication via network 102 is shown. For any given BIN there can be a number of associated PCNs. Server 122 can contain all the possible PCNs for a given BIN, and can have received the PCNs from BIN database 124. Server 126 can query server 122 in order to get a list of possible PCNs for that patient. In order to establish which is the correct PCN for that BIN, server 122 can perform a trial adjudication for each PCN until a valid claim is obtained.

The data can be sent in NCPDP format. Intermediary network 128 can route the data to the correct one or more PBM servers 130a and 130b using BIN information. For example, intermediary network 128 can call one or more of PBM servers 130 and route the data to it. A PBM server 130 can process the data and respond with a claim response. The claim response can identify whether the claim was successful or a failure. A successful claim indicates that a co-payment can be determined by the PBM server 130. A failure claim indicates that a co-payment could not be determined by the PBM server 130. The response is transmitted by PBM server 130 via intermediary network 128 to server 126. One or more responses can be obtained from one or more PBM servers at the same time or at different times. The responses can be provided fast enough such that they are eventually delivered to a user's device in real time. If the claim adjudicated successfully then the claim can be reversed and the PCN can be marked as being the correct one for that BIN/insurance combination.

FIG. 6 shows an exemplary architecture 600 in accordance with embodiments of the present disclosure that translates PBM responses to patient understandable information.

Specifically, architecture 600 includes device 104, server 106, server 126, server 132, and response database 136 from FIG. 1. Architecture 600 can take a claim response from a PBM server, such as server 130, and present it in a way that a patient can understand on device 104. An adjudication response from a PBM server (such as server 130) can be transmitted from server 126 to response database 136.

Server 132 can receive a response from a server 126. Server 132 can parse the response into its constituent parts and send those parts to a matching service. The matching service can use a set of previously parsed responses of response database 136 as well as a matching algorithm to determine the correct response to return to a device 104. This architecture can improve over time to give better responses by changes to the data made that can be made as time progresses. In some embodiments, feedback can be used to better determine the correct response (reinforcement learning) to learn to return more correct answers and deal with previously unseen data sets. Once the matching service has found its best responses it will return those to the server 132. The server 132 can then send the responses to a device 104 in a format that is readable by the device, and allows display of the information by device 104.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

The invention claimed is:

1. A computer architecture for real-time data processing, the architecture configured to:
   receive, by a first server, a trial adjudication request for a cost determination, the trial adjudication request including a request for an electronic calculation of a co-payment amount and a plurality of data sets obtained from a plurality of remote servers;
   verify, by the first server, the trial adjudication request using a security protocol, wherein a password token of the trial adjudication request is matched to a stored password token, and the stored password token is variable;
   transmit, by the first server, an adjudication command packet to a second server, the adjudication command packet including at least one data set of the plurality of data sets and a command for a claim determination;
   receive, by the first server, a response packet from the second server, the response packet, indicating a successful or failed claim determination performed by the second server and including claim data generated by the second server;
   determine, by the first server, that a successful claim determination was performed by the second server from the response packet;
   transmit, by the first server, a reversal request packet to the second server, the reversal request packet canceling the successful claim determination;
   update, by the first server, a decentralized electronic ledger to reflect that the claim determination was successful;
   perform, by the first server, the electronic calculation using the claim data generated by the second server, and generate a first result of the calculation; and
   transmit, by the first server, the first result to a third server configured to store the first result,
   wherein the first result is configured for display in real-time on a graphical user interface, and
   wherein the first result is a co-payment amount.

2. The architecture of claim 1, wherein the graphical user interface is of a mobile computing device.

3. The architecture of claim 2, wherein the first result is configured for display on a geographical map interface of the graphical user interface.

4. The architecture of claim 2, wherein the first result is configured for display on a list interface of the graphical user interface.

5. The architecture of claim 1, further configured to:
   receive, by the first server, a plurality of additional response packets indicating a successful or failed claim determination performed by a plurality of fourth servers and including claim data generated by the plurality of fourth servers;
   determine, by the first server, that additional successful claim determinations were performed by at least some of the fourth servers from the plurality of additional response packets;
   transmit, by the first server, additional reversal request packets to the fourth servers that performed the additional successful claim determinations, the additional reversal request packets canceling the successful claim determinations of the fourth servers;
   update, by the first server, the decentralized electronic ledger to reflect that the additional claim determinations were successful;
   perform, by the first, server, a plurality of electronic calculations using the claim data generated by the fourth servers, and generate a plurality of results of the calculations as second results; and transmit, the second results to the third server.

6. The architecture of claim 5, wherein the second results are configured for display on the graphical user interface of the mobile computing device along with the first result.

7. The architecture of claim 5, wherein the second results are each different.

8. The architecture of claim 5, wherein the second results are different to the first result.

9. The architecture of claim 5, wherein the plurality of data sets include location data generated by a global positioning system.

10. The architecture of claim 5, wherein the plurality of data sets include location data obtained due to an interaction with a graphical user interface of a mobile computing device.

11. The architecture of claim 1, wherein the password token of the trial adjudication request is variable.

12. The architecture of claim 11, wherein the password token of the trial adjudication request and the stored password token are varied on a periodic basis.

13. The architecture of claim 11, wherein the password token of the trial adjudication request and the stored password token are varied on a non-periodic basis.

14. The architecture of claim 1, wherein the adjudication command packet comprises at least one masked data structure that includes one or a combination of bits reflecting a pharmacy identification number, the pharmacy identification number identifying a particular pharmacy.

15. A method for real-time data processing comprising:
receiving, by a first server, a trial adjudication request for a cost determination, the trial adjudication request including a request for an electronic calculation of a co-payment amount, and a plurality of data sets obtained from a plurality of remote servers;
verifying, by the first server, the trial adjudication request, using a security protocol, wherein a password token of the trial adjudication request is matched to a stored password token, and the stored password token is variable;
transmitting, by the first server, an adjudication command packet to a second server, the adjudication command packet including at least one data set of the plurality of data sets and a command for a claim determination;
receiving, by the first server, a response packet from the second server, the response packet indicating a successful or failed claim determination performed by the second server and including claim data generated by the second server;
determining, by the first server, that a successful claim determination was performed by the second server from the response packet;
transmitting, by the first server, a reversal request packet to the second server, the reversal request packet canceling the successful claim determination;
updating, by the first server, a decentralized electronic ledger to reflect that the claim determination was successful;
performing, by the first server, the electronic calculation using the claim data generated by the second server, and generating a first result of the calculation; and
transmitting, by the first server, the first result to a third server configured to store the first result,
wherein the first result is configured for display in real-time on a graphical user interface, and
wherein the first result is a co-payment amount.

16. The method of claim 15, wherein the first result is configured for display on a graphical user interface of a mobile computing device.

17. The method of claim 16, wherein the first result is configured for display on a geographical map interface of the graphical user interface.

18. The method of claim 16, wherein the first result is configured for display on a list interface of the graphical user interface.

19. The method of claim 15 further comprising:
receiving, by the first, server, a plurality of additional response packets indicating a successful or failed claim determination performed by a plurality of fourth servers and including claim data generated by the plurality of fourth servers;
determining, by the first server, that additional successful claim determinations were performed by at least some of the fourth servers from the plurality of additional response packets;
transmitting, by the first server, additional reversal request packets to the fourth servers that performed the additional successful claim determinations, the additional reversal request packets canceling the successful claim determinations of the fourth servers;
updating, by the first server, the decentralized electronic ledger to reflect that the additional claim determinations were successful;
performing, by the first server, a plurality of electronic calculations using the claim data generated by the fourth servers, and generating a plurality of results of the calculations as second results; and
transmitting the second results to the third server.

* * * * *